United States Patent
Palombi et al.

(10) Patent No.: US 7,223,867 B2
(45) Date of Patent: May 29, 2007

(54) PREPARATION OF BENZOSUBERONYLPIPERIDINE COMPOUNDS

(75) Inventors: Giovanni Palombi, Milan (IT); Silvano Ronzoni, Milan (IT)

(73) Assignee: GlaxoSmithKline S.P.A., Verona (IT)

( * ) Notice: Subject to any disclaimer, the term of this patent is extended or adjusted under 35 U.S.C. 154(b) by 0 days.

(21) Appl. No.: 10/494,838

(22) PCT Filed: Nov. 5, 2002

(86) PCT No.: PCT/EP02/12356

§ 371 (c)(1),
(2), (4) Date: Oct. 8, 2004

(87) PCT Pub. No.: WO03/040099

PCT Pub. Date: May 15, 2003

(65) Prior Publication Data

US 2005/0059700 A1 Mar. 17, 2005

(30) Foreign Application Priority Data

Nov. 7, 2001 (GB) ................... 0126768.1

(51) Int. Cl.
C07D 211/06 (2006.01)
(52) U.S. Cl. .................. 546/205; 546/206; 546/207
(58) Field of Classification Search ................ 546/205, 546/206, 207
See application file for complete search history.

(56) References Cited

U.S. PATENT DOCUMENTS 5,157,129 A * 10/1992 Blacklock et al. ............ 549/23

FOREIGN PATENT DOCUMENTS

| WO | WO 00/27815 | * | 5/2000 |
| WO | WO0183454 A | | 11/2001 |

OTHER PUBLICATIONS

Ponzo et al, Tetra. Let. vol. 36 No. 50 pp. 9105-9108 (1995).*
Hett et al, CA 128:157888, (1998).*
Cho et al, CA 138:254887, (2002).*
March, Jerry, "Advanced Organic Chemistry", John Wiley & Sons, NY XP002232847, pp. 798-800 (1985).

Lane, Clinton F., Sodium Cyanoborohydride, a highly selective reducing agent for organic functional groups:, Database Accession No. 82:124186, XP002232848, Abstract & Synthesis (1975), (3), pp. 135-146.

* cited by examiner

Primary Examiner—Thomas McKenzie
Assistant Examiner—Raymond Covington
(74) Attorney, Agent, or Firm—Andrea L. Winslow; Theodore R. Furman, Jr.; Charles M. Kinzig

(57) ABSTRACT

Diastereoselective and enantioselective synthetic routes for the preparation of compounds of formula (I):

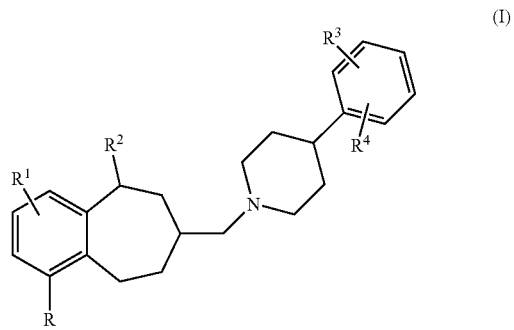

or derivatives thereof,
wherein:
R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, aryl$C_{1-6}$alkoxy, heteroaryl$C_{1-6}$alkoxy, amino$C_{1-6}$alkyl, ($C_{1-6}$alkyl)amino$C_{1-6}$alkyl, di($C_{1-6}$alkyl)amino$C_{1-6}$alkyl, aryl$C_{1-6}$alkylamino, heteroaryl$C_{1-6}$alkyamino;

$R^1$ is hydrogen or R;

$R^2$ is hydroxy, $C_{1-6}$alkoxy, amino, $C_{1-6}$alkylamino, di($C_{1-6}$alkyl)amino;

$R^3$ and $R^4$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$ alkoxy, $C_{1-6}$alkyl, amino, $C_{1-6}$alkylamino, or di($C_{1-6}$alkyl)amino; and wherein any alkyl group or the alkyl moiety of any group containing such a moiety may be substituted one or more times by halo.

7 Claims, No Drawings

PREPARATION OF BENZOSUBERONYLPIPERIDINE COMPOUNDS

This application claims the benefit of International Application Number PCT/EP02/12356 filed Nov. 5, 2002.

The present invention relates to novel diastereoselective and enantioselective synthetic routes to certain compounds, useful as ligands of the ORL-1 receptor.

A class of benzosuberonylmethylpiperidine derivatives is disclosed in International Patent Application, Publication Number WO 01/83454 (SmithKline Beecham SpA) as modulators of the ORL-1 receptor. A general synthetic methodology for preparing such compounds has also been disclosed in this patent application.

The present invention provides a novel and highly efficient method of synthesis for preparing both the diastereomers of compounds within the class disclosed in International Patent Application, Publication Number WO 01/83454 with high diastereomeric purity.

In another aspect, this invention also provides a novel synthetic route for preparing both the enantiomers of these compounds with very high enantiomeric purity.

Thus, the invention relates to the preparation of compounds of general formula (I):

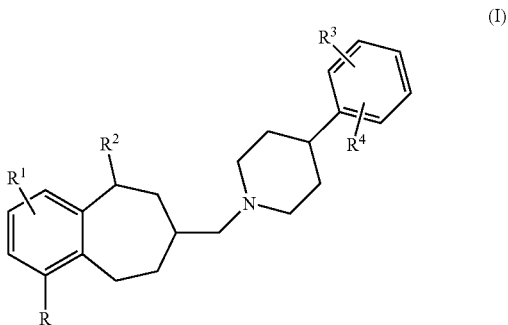

or derivatives thereof, wherein:

R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, aryl$C_{1-6}$alkoxy, heteroaryl$C_{1-6}$alkoxy, amino$C_{1-6}$alkyl, ($C_{1-6}$alkyl)amino$C_{1-6}$alkyl, di($C_{1-6}$alkyl)amino$C_{1-6}$alkyl, aryl$C_{1-6}$alkylamino, heteroaryl$C_{1-6}$alkylamino;

$R^1$ is hydrogen or R;

$R^2$ is hydroxy, $C_{1-6}$alkoxy, amino, $C_{1-6}$alkylamino, di($C_{1-6}$alkyl)amino;

$R^3$ and $R^4$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$alkoxy, $C_{1-6}$alkyl, amino $C_{1-6}$alkylamino, or di($C_{1-6}$alkyl)amino; and wherein any alkyl group or the alkyl moiety of any group containing such moiety may be substituted one or more times by halo.

In general formula (I), suitably, R is $C_{1-6}$alkenyl, $C_{1-6}$alkyl, halo, or $C_{1-6}$alkoxy. Favourably, R is vinyl, allyl, ethyl, methyl, fluoro, bromo, or methoxy. Preferably, R is methyl, fluoro, or bromo. More preferably, R is methyl.

Suitably, $R^1$ is hydrogen or methyl. Favourably, $R^1$ is hydrogen or 4-methyl.

Suitably, $R^2$ is hydroxy.

Suitably, $R^3$ is hydroxy$C_{1-6}$alkyl, halo, perhalo$C_{1-6}$alkyl, $C_{1-6}$alkyl, or hydrogen. Favourably, $R^3$ is hydroxymethyl, fluoro, trifluoromethyl, chloro, methyl, bromo, hydrogen. More favourably, $R^3$ is 2-hydroxymethyl, 2-F, 2-$CF_3$, 2-Cl, 2-Me, 3-Me, 2-Br, or hydrogen. Preferably, $R^3$ is 2-Cl, 2-F, 2-Me, or 2-Br. More preferably, $R^3$ is 2-Cl or 2-Me.

Suitably, $R^4$ is $C_{1-6}$alkyl, hydrogen, or halo. Favourably, $R^4$ is methyl, hydrogen, fluoro, or chloro. More favourably, $R^4$ is hydrogen, 6-Me, 3-F, 5-F, 6-F, or 6-Cl. Preferably, $R^4$ is hydrogen, 3-F, 6-Me, 6-F, or 6-Cl. More preferably, $R^4$ is 6-Me, 6-F, or 6-Cl.

Compounds of general formula (I) may exhibit stereoisomerism owing to the presence of two stereogenic centers at carbon C(5) and at carbon C(7). In dependence on the relative position of the substituent $R^2$ at carbon C(5) and of the substituent at carbon C(7), compounds of formula (I) may exist as two diastereomers, cis and trans. In addition, both the cis and the trans isomers exhibit optical isomerism, thus existing each as a couple of enantiomers. As a consequence, compounds of formula (I) may in principle exist as a mixture of a total of four isomers (two enantiomers of the cis form and two enantiomers of the trans form).

It has been found that, depending on the substituents R, $R^1$, $R^2$, $R^3$, $R^4$, one diastereomer can be more active as ORL-1 ligand than the other; moreover, it has been found that one enantiomer can be more active than the other antipode. Therefore, it is apparent that one of the four possible stereoisomers of a compound of formula (I) is generally endowed with a greater affinity than the three other isomers. Hence, there is need for a synthetic pathway which allows only one of the four possible stereoisomers to be obtained.

In International Patent Application, Publication Number WO 01/83454 it is reported that the two enantiomers of compounds of formula (I) can be separated through preparative chiral HPLC with the aid of a chiral stationary phase, the synthetic route to benzocycloheptane ligands, therein described, does not allow to obtain selectively only one of the two diastereomers, thus giving rise in most cases to diastereomeric cis/trans mixtures.

Therefore, in one aspect the present invention provides a diastereoselective synthetic route which affords selectively one diastereomer of compounds of formula (I) (referred to from here on as the diastereoselective synthesis or Process A). In another aspect the present invention provides an enantioselective synthetic route which provides selectively one enantiomer of compounds of formula (I) (referred to from here on as the enantioselective synthesis or Process B).

In the diastereoselective synthesis of this invention, a compound of formula (I) is prepared from a compound of formula (II) or (III)

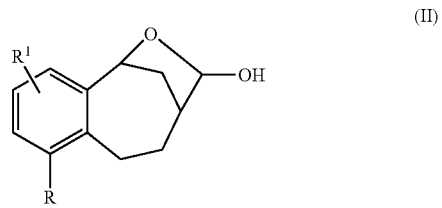

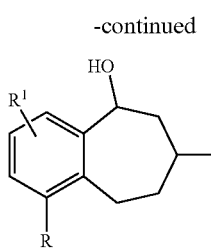

wherein:
R and $R^1$ are as hereinbefore defined for formula (I); by reacting a compound of formula (II) or (III) which is a single diastereoisomer or part of a mixture of diastereoisomers in which one diastereoisomer is predominant with a compound of formula (IV)

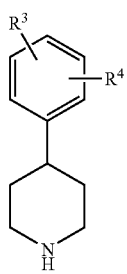

wherein:
$R^3$ and $R^4$ are as hereinbefore defined for formula (I); under reductive amination conditions with a suitable reducing agent, such as a modified borohydride or a metal hydride or a borane-containing reducing agent, or by catalytic hydrogenation.

A compound of formula (II) generally may exist in the cyclic form shown in the formula (II), or as an open form, as in the formula (III), or as a mixture of the two forms (II) and (III), depending upon the substituents R and $R^1$. Both the forms (II) and (III) are equally suitable to react with a compound of formula (IV).

In this reaction, typically a solution of a compound of formula (IV) in a suitable solvent is added to a solution of a compound of formula (II) or (III) in a suitable solvent, at a suitable initial temperature and is then stirred at a suitable reaction temperature for a suitable period of time. A suitable solvent is an alcohol, a chlorinated hydrocarbon, an ether or a nitrile. A preferable solvent is methanol, ethanol, isopropanol, acetonitrile, diethyl ether, tetrahydrofuran or 1,2-dichloroethane. A suitable temperature for initially mixing the reactants is in the range 20-25° C. A suitable reaction temperature is in the range from 20° C. to the reflux temperature of the solvent; a suitable period of time for the reaction is 0.5-5 hours. Then, a suitable reducing agent is added. A suitable reducing agent is sodium borohydride, sodium cyanoborohydride, sodium triacetoxyborohydride, lithium aluminium hydride, borane, or hydrogen in the presence of a metal catalyst such as palladium, nickel, or platinum. A suitable rate of addition is over 5-30 minutes, a suitable initial temperature is 0-5° C., a suitable reaction temperature is from 15° C. to the reflux temperature of the solvent, a suitable period of time for the reaction is 1-12 hours. The mixture may then be quenched, filtered if necessary, then if necessary extracted with a suitable organic solvent. Afterwards, the solvent is evaporated and the crude product purified. A suitable quenching medium is water, a suitable organic solvent for the extraction is ethyl acetate or dichloromethane. Conventional methods of cooling and heating such as ice/salt baths and electric heating mantles may be employed. Conventional methods of purification such as flash chromatography, crystallisation or trituration may be employed.

In a preferred working of the diastereoselective synthesis, a solution of the compound of formula (IV) in methanol is added dropwise at room temperature into a solution of a compound of the formula (II) or (III) in methanol. The mixture is heated at 50° C. for 2 hours and then allowed to cool at room temperature. Then, sodium borohydride is added over a 10-minutes period, at 0° C. and stirring at ambient temperature is maintained overnight. After quenching with water and extraction with ethyl acetate, the organic phase is collected, dried with, for example, sodium sulphate and the solvent is removed by evaporation. The crude product is finally purified by flash chromatography. Compounds of formula (IV) may be synthesized as described by Perregard, *J. Med. Chem.*, 38, 1998,(1995) and Guzikowski, *J. Med. Chem.*, 43, 984,(2000).

Compounds of formula (II) and (III) may be prepared from compounds of formula (V)

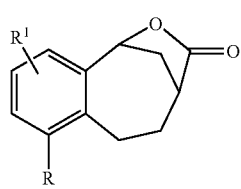

wherein:
R and $R^1$ are as hereinbefore defined for formula (I); by reduction with a suitable reducing agent such as an hindered aluminum hydride, or using a titanocene complex (as described by Verdaguer, *J. Org. Chem.*, 62, 8522, (1997)).

In general, a compound of formula (II) or (III) may be suitably prepared as follows: to a solution of a compound of formula (V) in a suitable dry solvent at a suitable initial temperature, a suitable reducing agent is added under a suitable inert atmosphere and the mixture is stirred at a suitable reaction temperature for a suitable period of time. A suitable dry solvent is diethyl ether, dichloromethane, toluene. A suitable initial temperature is in the range −78° to 0° C. A suitable reducing agent is an hindered aluminum hydride such as diisobutylaluminum hydride, or sodium bis(2-methoxyethoxy)aluminum hydride, or sodium bis(2-methoxyethoxy)ethoxyaluminum hydride, or lithium tri-t-butoxyaluminum hydride. Preferably, the reducing agent is diisobutylaluminum hydride or sodium bis(2-methoxyethoxy)ethoxyaluminium hydride. A suitable inert atmosphere is a nitrogen atmosphere, a suitable reaction temperature is in the range −78° C. to 0° C., a suitable period of time is 0.5-3 hours. The reaction mixture is then treated with a suitable quenching agent at a suitable temperature, allowed to warm at ambient temperature and stirred for a suitable period of time. The mixture is subsequently partitioned between water and a suitable organic solvent, the organic layer is dried over, for example, sodium sulphate, then filtered and concentrated under reduced pressure. The crude product may be purified by a suitable conventional method such as chromatography, crystallisation, trituration or filtration through a short bed of a suitable adsorbent. A suitable quenching agent is methanol, water or a saturated aqueous solution of sodium potassium tartrate tetrahydrate. A suitable temperature for the quenching is −78° C. to 0° C. A suitable period of time is 0.5-2.5 hours. A suitable organic solvent is ethyl acetate or toluene. A suitable adsorbent is silica gel.

Preferably, a compound of formula (V) is dissolved in dry toluene under nitrogen, the solution is cooled at −60° C. and a solution of diisobutylaluminium hydride in hexane is added dropwise. After stirring for 1 hour at −60° C., the mixture is quenched subsequently with methanol and then with a saturated solution of Rochelle's salt (sodium potassium tartrate tetrahydrate) in water. The mixture is then allowed to warm at ambient temperature, kept under stirring for 2 hours and finally partitioned between water and ethyl acetate. The combined organic extracts are dried over sodium sulphate, filtered, evaporated under reduced pressure. Filtration of the resulting crude product on a short bed of silica gel affords the pure compound of formula (II) or (III).

A compound of formula (V) may be prepared from a compound of formula (VI)

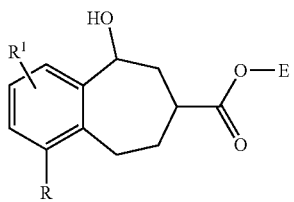

(VI)

wherein:

R and $R^1$ are as hereinbefore defined for formula (I) and E is $C_{1-6}$alkyl; with an agent suitable to promote the intramolecular lactonization such as an inorganic or organic base or such as an inorganic or organic acid.

Two different processes to perform the lactonization are described below, in dependence on whether an inorganic or organic base is used or an inorganic or organic acid is used.

In general, if an inorganic or organic base is used, a solution of the compound of formula (VI) in a suitable solvent, is added to a solution or a suspension of a suitable agent of lactonization in a suitable dry solvent at a suitable initial temperature, under a suitable inert atmosphere and stirring of the mixture is maintained for a suitable period of time at a suitable reaction temperature. A suitable solvent for both the compound of formula (VI) and the agent of lactonization is an ether such as tetrahydrofuran, diethyl ether. A suitable agent of lactonization is an inorganic base such as sodium hydride, sodium ethoxide, sodium methoxide or an organic base such as an amine, a preferable amine is pyrrolidine or piperidine. A suitable initial temperature is 15-25° C., a suitable inert atmosphere is nitrogen, a suitable period of time is 1-5 hours, a suitable reaction temperature is in the range from 15° C. to the reflux temperature of the solvent. Then, the mixture is cooled to a suitable temperature, treated with a suitable quenching medium and extracted with a suitable organic solvent, the combined organic extracts are dried for example over magnesium sulphate, filtered and concentrated in vacuo. The crude product is a mixture of a compound of formula (V) and a compound of formula (VI). The latter is present exclusively as trans isomer. The compound of formula (V) and the compound of formula (VI) are separated by means of a suitable separation technique such as flash chromatography, crystallization, distillation, trituration. A suitable temperature for quenching is 0-5° C. A suitable quenching medium is water or methanol. A suitable organic solvent is diethyl ether. A suitable separation technique is flash chromatography.

Conventional means of heating and cooling, for example ice/baths and electric heating mantles, may be employed.

Preferably, a solution of the compound of formula (VI) in dry tetrahydrofuran is added at 25° C. to a suspension of sodium hydride in dry tetrahydrofuran, under a nitrogen atmosphere. After stirring at ambient temperature for 2.5 hours, the mixture is quenched with water at 0° C., extracted with diethyl ether, the organic layer is dried, filtered, evaporated under reduced pressure. Flash chromatography on silica gel allows to separate the lactone (V) and the compound (VI) as trans isomer.

On the other hand, if an inorganic or organic acid is used, to a solution of a compound of formula (VI) in a suitable solvent a suitable agent of lactonization is added at a suitable initial temperature. The mixture is stirred at a suitable reaction temperature for a suitable time period, then subsequently water, a suitable basic aqueous solution and a suitable organic solvent is added; the organic layer is washed twice with the same suitable basic aqueous solution as above, then collected, dried over magnesium sulphate for example and concentrated in vacuo. The crude product is a mixture of a compound of formula (V) and a compound of formula (VI). The latter is present exclusively as trans isomer. The compound of formula (V) and the compound of formula (VI) are separated by means of a suitable separation technique such as flash chromatography, crystallization, distillation, trituration. A suitable solvent is dichloromethane, 1,2-dimethoxyethane or methanol. A suitable agent of lactonization is p-toluenesulphonic acid, pyridinium p-toluenesulphonate, hydrochloric acid, trifluoroacetic acid. A preferred agent of lactonization is p-toluenesulphonic acid or pyridinium p-toluenesulphonate. A suitable initial temperature is 0-25° C. A suitable reaction temperature is in the range from 0° C. to the reflux temperature of the solvent. A suitable time period is 0.5-10 hours, a suitable basic aqueous solution is a saturated solution of sodium bicarbonate in water, a suitable organic solvent is diethyl ether. A suitable separation technique is flash chromatography.

Preferably, to a solution of a compound of formula (VI) in 1,2-dimethoxyethane, p-toluenesulphonic acid is added portionwise at ambient temperature and the mixture is stirred at 25° C. for 10 hours. Water, a saturated solution of sodium bicarbonate in water and diethyl ether are added in the order, the organic layer is collected, repeatedly washed with a saturated solution of sodium bicarbonate in water and finally dried, filtered and concentrated in vacuo. Flash chromatography on silica gel allows then to separate the lactone (V) and the compound (VI) as trans isomer.

A compound of formula (VI) may be synthesized from a compound of formula (VII) such as:

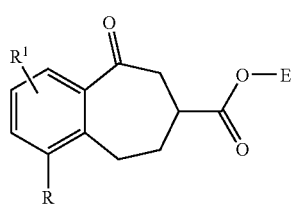

(VII)

wherein:
R and $R^1$ are as hereinbefore defined for formula (I) and E is $C_{1-6}$alkyl; through reduction with a suitable reducing agent. Suitable reducing agents are metallic borohydrides such as sodium borohydride and potassium borohydride, or borane-containing reducing agents such as borane-methyl sulfide, borane-tetrahydrofuran, borane-pyridine and diborane itself, or alane, or hindered alkyl-substituted borohydrides such as lithium tri-(sec-butyl)-borohydride, sodium tri-(sec-butyl)-borohydride, potassium tri-(sec-butyl)-borohydride, or hydrogen in presence of a metallic catalyst such as Ni, Pd, Pt.

In general, to a compound of formula (VII) in a suitable organic solvent under a suitable inert atmosphere, a suitable reducing agent is added at a suitable initial temperature. A suitable inert atmosphere is nitrogen. A suitable reducing agent is borane-methyl sulfide, sodium borohydride or lithium tri-(sec-butyl)-borohydride. A suitable organic solvent is dry diethyl ether or dry tetrahydrofuran if borane-methyl sulfide or lithium tri-(sec-butyl)-borohydride is used as a reducing agent, otherwise is ethanol if sodium borohydride is used as a reducing agent. A suitable initial temperature is in the range from –20° C. to 0° C. After stirring at a suitable reaction temperature for a suitable reaction time, the reaction mixture is treated with a suitable quenching agent at a suitable quenching temperature. Then, water and a suitable organic solvent are added, organic layer is separated, dried over sodium sulphate for instance, and finally concentrated in vacuo. A suitable reaction temperature is in the range from –20° C. to 25° C. A suitable reaction time is 1-12 hours. A suitable quenching agent is water or methanol. A suitable quenching temperature is 0° C.-5° C. A suitable organic solvent for extraction is dichloromethane. Purification of the crude product may be carried out through the conventional means of purification such as silica gel chromatography, crystallization, trituration. Conventional methods of cooling and heating such as ice/salt baths and electric heating mantles may be employed during the procedure above.

Preferably, neat borane-methyl sulfide complex is dropped into a solution of a compound of formula (VII) in dry tetrahydrofuran, under nitrogen, at 0° C. After stirring overnight at 25° C., the reaction mixture is cooled at 0° C., quenched with methanol and concentrated in vacuo. The residue is redissolved in methanol and concentrated in vacuo again. This operation is repeated twice, then the resulting residue is purified by flash chromatography on silica gel to give the pure compound of formula (VI) as an equimolar mixture of cis and trans hydroxyesters.

A compound of formula (VII) can be suitably prepared from a compound of formula (VIII)

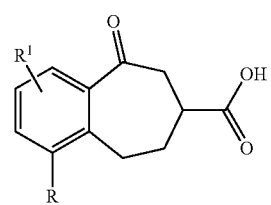

(VIII)

wherein:
R and $R^1$ are as hereinbefore defined for formula (I); by formation of the ester with a suitable alcohol under the conventional conditions of esterification.

Suitable conditions are Fischer esterification method (boiling the alcohol and the acid in presence of a mineral acid such as sulphuric acid, with azeotropic distillation), or activation of the acid with a suitable activating agent such as HOBT (1-hydroxy-benzotriazole), HOAT (1-hydroxy-7-aza-benzotriazole), HOS (N-hydroxy-succinimide) in presence of a condensating agent such as DCC (dicyclohexyl-carbodiimide) or EDC (N-ethyl-N'-(3-dimethylaminopropyl)carbodiimide), followed by addition of the alcohol. Suitable conditions are also preformation of the acyl halide through a suitable halogenating agent such as oxalyl chloride or thionyl chloride, followed by addition of the alcohol. Alternatively, suitable conditions are condensation of the acid and the alcohol with dicyclohexylcarbodiimide and 4-(dimethylamino)pyridine.

In the procedure hereinafter reported, both halogenating agents and activating agents (as defined above) are referred generally as esterification agents. In general, to a solution of a compound of formula (VIII) in a suitable organic solvent is added a suitable esterification agent at a suitable initial temperature. A suitable organic solvent is dry dichloromethane, a suitable esterification agent is thionyl chloride or oxalyl chloride, a suitable initial temperature is in the range 0° C.-25° C. The mixture is maintained under stirring for a suitable period of time at a suitable reaction temperature and concentrated in vacuo. To the residue dissolved in a suitable solvent, a suitable alcohol is added at a suitable second temperature. A suitable period of time is 2-12 hours, a suitable reaction temperature is from 15° C. to the reflux temperature of the solvent, a suitable solvent is dichloromethane, a suitable alcohol is methanol, ethanol, propanol, butanol, pentanol, hexanol for instance, a suitable second temperature is 0° C.-5° C. After stirring at a suitable temperature for a suitable period of time, water is added, as well as a suitable extraction solvent; repeated extraction of the aqueous layer, drying of the organic extracts over sodium sulphate and evaporation under reduced pressure afford a crude product which is purified by the conventional means such as flash chromatography, trituration, crystallization. A suitable temperature is from 15° C. to the reflux temperature of the solvent, a suitable period of time is 0.5-2 hours, a suitable extraction solvent is dichloromethane, a suitable means of purification is flash chromatography.

In a preferred aspect, to a solution of a compound of formula (VIII) in dry dichloromethane, oxalyl chloride is added dropwise at 0° C. The mixture is stirred overnight at room temperature, concentrated in vacuo and to the residue dissolved in dichloromethane, methanol is added at 0° C.

After stirring for 1.5 hours at ambient temperature, the mixture is diluted with water and extracted with dichloromethane; the organic layer is dried over sodium sulphate, filtered and concentrated in vacuo to give a crude product which is purified by flash chromatography on silica gel.

Compounds of formula (VIII) may be obtained according to Bowman, *Tetrahedron*, 48, 4027,(1992), or Hasegawa, *Tetrahedron Lett.*, 39, 4059,(1998), or may be prepared as described in PCT/EP01/04943.

The diastereoselective synthesis may be summarised in the following reaction scheme (Scheme 1):

Scheme 1
PROCESS A-diastereoselective synthesis

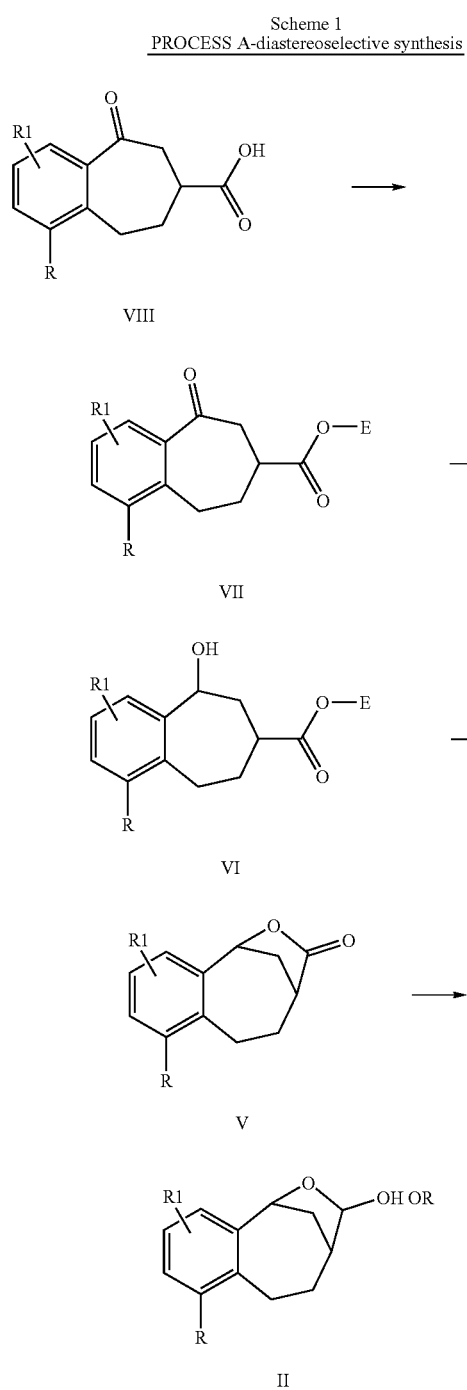

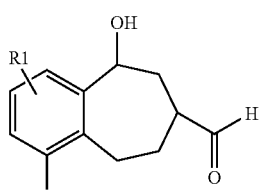

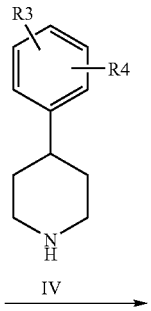

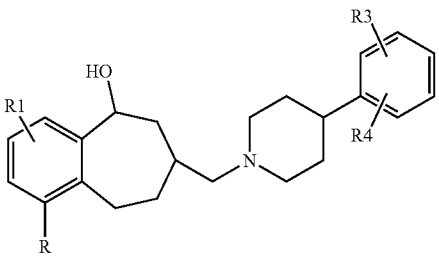

The final compound of the reaction scheme of Process A is a compound of formula (I) in which $R^2$ is OH.

To obtain other indicated values for $R^2$ the process of the invention includes conversion of one compound of formula (I) into another compound of formula (I) by converting one group $R^2$ into another group $R^2$ using conventional procedures.

The above mentioned conversion may be carried out using any appropriate method under conditions determined by the particular groups chosen. Suitable conversions of one group $R^2$ into another group $R^2$ include:

(i) converting a group $R^2$ which represents hydroxy into a group $R^2$ which represents alkoxy; such a conversion may be carried out using a conventional alkylation procedure, for example treating an appropriately protected compound of formula (I) with a strong base such as sodium hydride and alkylating the resultant alkoxide anion with a suitable alkylating agent such as an alkyl halide, and;

(ii) converting a group $R^2$ which represents hydroxy into a group $R^2$ which represents amino, alkylamino, or dialkylamino; such a conversion may be carried out using a conventional dehydroxyamination procedure, for example treating an appropriately protected compound of formula (I) wherein $R^2$ is hydroxy with an activating agent such as a methanesulphonyl halide or a p-toluenesulphonyl halide to transform the hydroxy group $R^2$ into the corresponding methanesulphonate or p-toluenesulphonate respectively and thereafter reacting the activated compound with an amine of formula $R^5R^6NH$, wherein $R^5$ and $R^6$ are each independently hydrogen or C1-6alkyl, in the presence of a hindered base such as triethylamine.

In the sequence of Process A, the key feature which allows discrimination between the cis and trans diastereoisomers is the formation of the intermediate lactone compound of formula (V). This intermediate forms another aspect of this invention as do all novel intermediates formed in the course of Process A.

Also of special importance in this invention for discrimination between the cis and trans diastereoisomers are the processes indicated above for preparation of compounds of formula (V) from compounds of formula (VI) and the preparation of compounds of formulae (II) and (III) from compounds of formula (V).

In the enantioselective synthesis of this invention, a compound of formula (I) is prepared from a compound of formula (II) or (III)

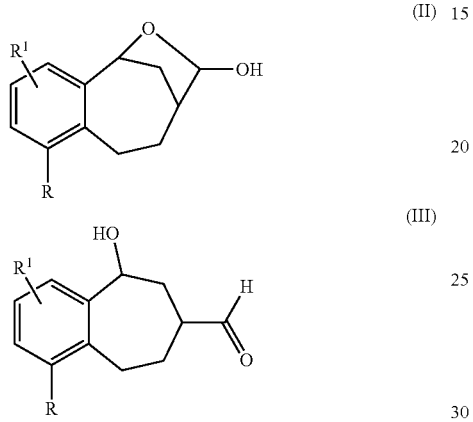

wherein:

R and $R^1$ are as hereinbefore defined for formula (I); by reacting a compound of formula (II) or (III) which is a single enantiomer or part of a mixture of enantiomers in which one enantiomer is predominant with a compound of formula (IV)

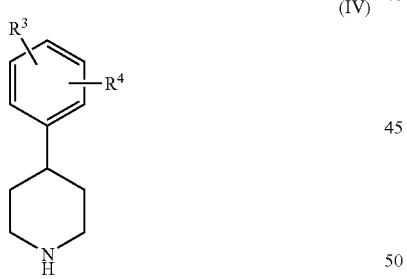

wherein:

$R^3$ and $R^4$ are as hereinbefore defined for formula (I); under reductive amination conditions with a suitable reducing agent, such as a modified borohydride or a metal hydride or a borane-containing reducing agent, or by catalytic hydrogenation.

The compounds of formulae (II) and (III) may be obtained as a single enantiomer, or mixture of enantiomers in which one enantiomer is predominant, by a suitable modification of the sequence of Process A above, to include an enantioselective process step. Suitably this is achieved by an enantioselective reduction of a compound of formula (VII), and then following the sequence of Process A as given above.

In accordance with this invention, the enantioselective reduction of a compound of formula (VII) may be accomplished with a suitable borane-containing reducing agent in presence of a suitable chiral auxiliary, such as one of the chiral oxazaborolidine derivatives reported below:

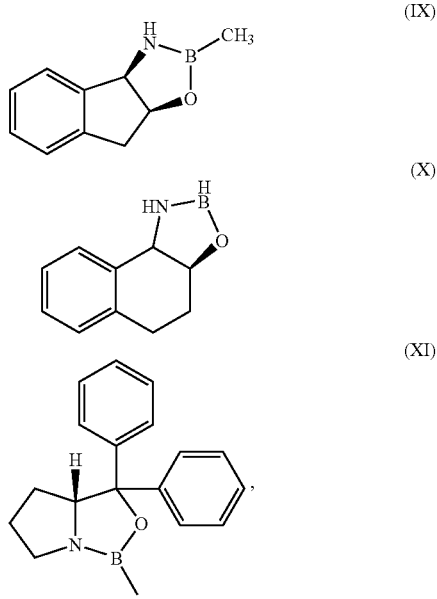

and their antipodes; the chiral oxazaborolidines (IX), (X), (XI) are either commercially available or may be prepared as described by Corey, *J. Am Chem. Soc.*, 109, 5551, (1987), by Hong, *Tetr. Lett.*, 35, 6631,(1994) and by Hett, *Tetr. Lett.*, 39, 1705,(1998). A suitable borane-containing reducing agent is borane-dimethyl sulfide, borane-tetrahydrofuran, borane-pyridine, borane-diethylaniline, catechol-borane.

Two different protocols for performing the enantioselective reduction of a compound of formula (VII) may be applied, indicated below as Protocol A and Protocol B.

Protocol A. If this protocol is applied, formation of a chiral borane-oxazaborolidine complex, such as (XII), prior to the enantioselective reduction is necessary. A complex of formula (XII) (or its antipode) may be prepared as described by Mathre, *J. Org. Chem.*, 58, 2880,(1993).

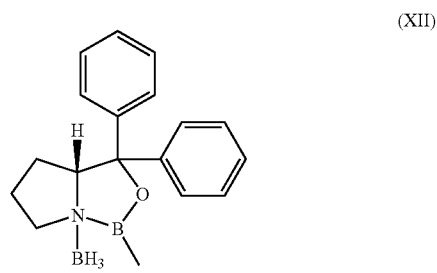

Moreover, two different experimental procedures may be applied to perform the asymmetric reduction (denoted as Protocol A' and Protocol A").

In the Protocol A', a suitable catalytic amount of a chiral borane-oxazaborolidine complex such as (XII) is added to a suitable solvent cooled at a suitable initial temperature, under a suitable inert atmosphere, and stirred until dissolution. A suitable amount of a suitable borane-containing species is added dropwise. Then, a solution of a compound of formula (VII) in a suitable solvent is dropped into the reaction mixture over a suitable period of time, at a suitable second temperature and then the mixture is stirred at that temperature for a suitable reaction time. A suitable catalytic amount of a chiral borane-oxazaborolidine complex is in the range from 0.05 eq to 0.20 eq. A suitable solvent is dichloromethane or tetrahydrofuran or toluene. A suitable initial temperature is in the range from −40° C. to −20° C. A suitable inert atmosphere is a static argon atmosphere. A suitable amount of borane-containing species is in the range 1 eq to 2 eq. A suitable borane-containing species is borane-dimethyl sulfide, borane-tetrahydrofuran, borane-pyridine, borane-diethylaniline, catechol-borane. A suitable period of time for the addition of (VII) is 10-50 minutes. A suitable second temperature is −50° C.-0° C. A suitable reaction time is 0.5-3 hours. Then, the mixture is treated with a suitable quenching medium at a suitable temperature, allowed to warm to room temperature and stirred at room temperature for a suitable period of time. Then, the mixture undergoes the following sequence of evaporation-dilution: the solvent is evaporated under reduced pressure, then the residue is diluted with a suitable solvent and concentrated in vacuo again. This sequence is repeated three-four times. A suitable quenching medium is methanol. A suitable temperature is −50° C. -0° C. A suitable period of time is 2-12 hours. A suitable solvent is methanol. The crude product is a mixture of a compound of formula (V) and a compound of formula (VI), as hereinbefore defined. The latter is present exclusively as trans isomer. The compound of formula (V) and the compound of formula (VI) are separated by means of a suitable separation technique such as flash chromatography, crystallization, distillation, trituration.

The enantiomeric excesses for both the compound of formula (V), i.e. the lactone, and the compound of formula (VI), i.e. the tans-hydroxy ester, are evaluated by means of a suitable analytical technique, such as chiral HPLC.

In the Protocol A", a suitable stoichiometric amount of a chiral borane-oxazaborolidine complex such as (XII) is added to a suitable solvent cooled at a suitable initial temperature, under a suitable inert atmosphere, and stirred until dissolution. Then, a solution of a compound of formula (VII) in a suitable solvent is dropped into the reaction mixture over a suitable period of time, at a suitable second temperature and then the mixture is stirred at that temperature for a suitable reaction time. A suitable stoichiometric amount of a chiral borane-oxazaborolidine complex is in the range from 1 eq to 2 eq. A suitable solvent is dichloromethane or tetrahydrofuran or toluene. A suitable initial temperature is in the range from −40° C. to −20° C. A suitable inert atmosphere is a static argon atmosphere. A suitable period of time for the addition of (VII) is 10-50 minutes. A suitable second temperature is −50° C.-0° C. A suitable reaction time is 0.5-3 hours. Afterwards, the mixture is treated with a suitable quenching medium at a suitable temperature, allowed to warm to room temperature and stirred at room temperature for a suitable period of time. Then, the mixture undergoes the following sequence of evaporation-dilution: the solvent is evaporated under reduced pressure, then the residue is diluted with a suitable solvent and concentrated in vacuo again. This sequence is repeated three-four times. A suitable quenching medium is methanol. A suitable temperature is from −50° C. to 0° C. A suitable period of time is 2-12 hours. A suitable solvent is methanol. The crude product is a mixture of a compound of formula (V) and a compound of formula (VI), as hereinbefore defined. The latter is present exclusively as trans isomer. The compound of formula (V) and the compound of formula (VI) are separated by means of a suitable separation technique such as flash chromatography, crystallization, distillation, trituration.

The enantiomeric excesses for both the compound of formula (V), i.e. the lactone, and the compound of formula (VI), i.e. the trans-hydroxy ester, are evaluated by means of a suitable analytical technique, such as chiral HPLC.

In a preferred aspect, a borane-oxazaborolidine complex of formula (XII) is dissolved in dry dichloromethane at −20° C. under a static atmosphere of argon. A solution of a compound of formula (VII) in dry dichloromethane is dropped into the reaction mixture at −20° C., over a 20 minutes period. The mixture is stirred at −20° C. for 1 hour and, without warming, methanol precooled at −20° C. is added. The solution is allowed to warm at room temperature, stirred for 2.5 hours, concentrated in vacuo. The resulting residue is dissolved in methanol and concentrated in vacuo again (this operation is repeated three times). Flash chromatography on silica gel affords a compound of formula (VI), i.e. the trans hydroxy-ester, and a compound of formula (V), i.e. the lactone. Subsequent chiral HPLC analysis enables to assess the enantiomeric excesses of the trans hydroxy ester and of the lactone, above isolated.

Protocol B If protocol B is applied to carry out the enantioselective reduction of a compound of formula (VII), no preformation of a borane-oxazaborolidine complex is required, but a borane-containing species (as hereinbefore defined) is added to a solution of an oxazaborolidine such as (IX), (X), (XI) prior to addition of the compound (VII).

In general, to a solution of a suitable oxazaborolidine in a suitable solvent, under a suitable inert atmosphere, a suitable borane-containing species is added dropwise at a suitable initial temperature. A solution of a compound of formula (VII) in a suitable second solvent is then dropped into the reaction mixture and stirring is maintained for a suitable period of time at a suitable reaction temperature. A suitable oxazaborolidine is for instance (IX), (X), (XI). A suitable solvent is tetrahydrofuran or dichloromethane. A suitable inert atmosphere is an argon atmosphere. A suitable borane containing species is borane-dimethyl sulfide, borane-tetrahydrofuran, borane-pyridine, borane-diethylaniline, catechol-borane. A suitable initial temperature is −20° C.-0° C. A suitable second solvent is tetrahydrofuran or dichloromethane. A suitable period of time is in the range from 10 minutes to 2 hours. A suitable reaction temperature is −20° C.-25° C. Then, the mixture is quenched with a suitable quenching medium at a suitable quenching temperature, allowed to warm to room temperature and stirred at room temperature for a suitable period of time. Then, the mixture undergoes the following sequence of evaporation-dilution: the solvent is evaporated under reduced pressure, then the residue is diluted with a suitable solvent and concentrated in vacuo again. This sequence is repeated three-four times. A suitable quenching medium is methanol. A suitable quenching temperature is −20° C.-0° C. A suitable period of time is 1-12 hours. A suitable solvent is methanol. The crude product is a mixture of a compound of formula (V) and a compound of formula (VI), as hereinbefore defined. The latter is present exclusively as trans isomer. The compound of formula (V) and the compound of formula (VI) are separated by means of a suitable separation technique such as flash chromatography, crystallization, distillation, trituration.

The enantiomeric excesses for both the compound of formula (V), i.e. the lactone, and the compound of formula (VI), i.e. the trans-hydroxy ester, are evaluated by means of a suitable analytical technique, such as chiral HPLC.

The enantioselective reduction of compound (VII), described above, is the key-step of the enantioselective synthesis, providing both the compound (VI), i.e. the trans-hydroxy ester, and the compound (V), i.e. the lactone, in enantiomeric excesses generally greater than 98%. Enantiomerically pure lactone (V) subsequently undergoes reduction to a compound of formula (II) or (III), as hereinbefore defined, following the same experimental procedure reported for the diastereoselective synthesis or Process A. Afterwards, reacting a compound of formula (IV), as hereinbefore defined, with the enantiomerically pure compound (II) or (III), according to the same experimental procedure reported for the diastereoselective synthesis or Process A, a compound of formula (I) enantiomerically pure is finally obtained. The enantiomeric purity of the final compound (I) is evaluated through chiral HPLC analysis and, in any case, the enantiomeric excess observed for the final compound (I) is identical to the ee observed for the lactone (V), after the enantioselective reduction: no epimerization or racemization occurs during the last two steps reported above.

As has previously been mentioned with reference to International Patent Application, Publication Number WO 01/83454,the contents of which are incorporated herein by reference, compounds of formula (I) are ligands of the ORL-1 receptor.

Accordingly, another aspect of the present invention provides a method of modulating the ORL-1 receptor activity in a human or animal patient in need thereof, which method comprises administering to the human or animal patient an effective amount of a compound of formula (I) or a pharmaceutically acceptable derivative thereof as a diastereoisomer or entantiomer obtainable or obtained by the processes of this invention.

In a further aspect of the present invention there is provided the use of a compound of formula (I), or a pharmaceutically acceptable derivative thereof as a diastereoisomer or entantiomer obtainable or obtained by the processes of this invention, in the manufacture of a medicament for modulating the ORL-1 receptor activity in a human or animal patient.

Said compounds of formula (I) may be agonists or antagonists of the ORL-1 receptor.

Accordingly, in a further aspect, the present invention provides the use of a compound of formula (I), or a pharmaceutically acceptable derivative thereof as a diastereoisomer or entantiomer obtainable or obtained by the processes of this invention, for the manufacture of a medicament as an analgesic for the treatment of, for example, acute pain; chronic neuropathic or inflammatory pain including post herpetic neuralgia; neuralgia; diabetic neuropathy and post stroke pain; osteoarthritis/back pain; painful pregnancy labour; and therapy of opioid tolerance and dependence.

In an additional aspect, the present invention provides the use of a compound of formula (I), or a pharmaceutically acceptable derivative thereof as a diastereoisomer or entantiomer obtainable or obtained by the processes of this invention, for the manufacture of a medicament for the treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic hormone (SIADH); adult respiratory distress syndrome (ARDS); congestive heart failure; cirrhosis with ascites; sexual dysfunctions including impotence and frigidity; and altered pulmonary function, including chronic obstructive pulmonary disease.

In yet a further aspect, the present invention provides the use of a compound of formula (I), or a pharmaceutically acceptable derivative thereof as a diastereoisomer or entantiomer obtainable or obtained by the processes of this invention, for the manufacture of a medicament for the treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion.

Accordingly, in a further aspect, there is provided a method of treatment of acute pain; chronic neuropathic or inflammatory pain including post herpetic neuralgia; neuralgia; diabetic neuropathy and post stroke pain; osteoarthritis/back pain; painful pregnancy labour; and therapy of opioid tolerance and dependence, which method comprises the administration of a compound of formula (I), or a pharmaceutically acceptable derivative thereof as a diastereoisomer or entantiomer obtainable or obtained by the processes of this invention, to the mammal in need thereof.

In a further aspect, there is provided a method of treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic hormone (SIADH); adult respiratory distress syndrome (ARDS); congestive heart failure; cirrhosis with ascites; sexual dysfunctions including impotence and frigidity; and altered pulmonary function, including chronic obstructive pulmonary disease, which method comprises the administration of a compound of formula (I), or a pharmaceutically acceptable derivative thereof as a diastereoisomer or entantiomer obtainable or obtained by the processes of this invention, to the mammal in need thereof.

In yet a further aspect, there is provided a method of treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion, which method comprises the administration of a compound of formula (I), or a pharmaceutically acceptable derivative thereof as a diastereoisomer or entantiomer obtainable or obtained by the processes of this invention, to the mammal in need thereof.

Administration of a compound in accordance with the invention for treatment of the conditions mentioned above may be carried out as disclosed in the above mentioned International Patent Application, Publication Number WO 01/83454.

The processes and intermediates of the present invention are illustrated by the following Examples and Preparations. However, it should be understood that the invention is not limited to the specific details of these Examples and Preparations which are given for exemplification purposes only.

Note: the abbreviations used to describe the peak shapes throughout this specification are as follows: s, singlet; d, doublet; t, triplet; m, multiplet; br, broad.

DIASTEREOSELECTIVE SYNTHESIS

PREPARATION 1

(±)-1-methyl-5-oxo-6,7,8,9-tetrahydro-5H-benzocycloheptene-7-carboxylic acid methyl ester To a solution of 1-methyl-5-oxo-6,7,8,9-tetrahydro-5H-benzocycloheptene-7-carboxylic acid (5 g, 22.91 mmol) in dry dichloromethane (DCM) (15 mL), oxalyl chloride (6 mL, 68.75 mmol) was added dropwise at 0° C. The reaction mixture was stirred overnight at room temperature, concentrated in vacuo and to the residue dissolved in DCM (30 mL), methanol (15 mL) was added at 0° C. After stirring 1.5 h at room temperature, the mixture was diluted with water (60 mL) and extracted with DCM (100 mL), the organic layer was dried over $Na_2SO_4$, filtered and concentrated in vacuo to give 6.0 g of a yellow oil. Purification by flash chromatography on silica gel (hexane/diethyl ether: 8/2) afforded the title compound as a pale yellow oil (5.6 g, 94%).

MS m/z (EI+): 232 (M+); 201; 173.

$^1$H NMR (300 MHz, $CDCl_3$): Δ 7.43 (1H, d), 7.30 (1H, d), 7.18 (1H, dd), 3.62 (3H, s), 3.37 (3H, s), 3.06–2.95 (3H, m), 2.92–2.78 (2H, m), 2.29–2.02 (2H, m).

PREPARATION 2

(±)-6-methyl-12-oxa-tricyclo[8.2.1.0]trideca-2,4,6-trien-11-one and (±)-trans-1-methyl-5-hydroxy-6,7,8,9-tetrahydro-5H-benzocycloheptene-7-carboxylic acid methyl ester Borane-methyl sulfide (2.25 mL, 22.5 mmol) was dropped into a solution of (±)-1-methyl-5-oxo-6,7,8,9-tetrahydro-5-benzocycloheptine-7-carboxylic acid methyl ester (5.6 g, 22.68 mmol) in dry tetrahydrofuran at 0° C., under nitrogen. After stirring overnight at 25° C., the reaction mixture was cooled at 0° C., quenched with methanol (80 mL) and concentrated in vacuo. The residue was redissolved in methanol and concentrated again (this operation was repeated twice) and the resulting residue was purified by flash chromatography (silica gel, DCM/ethyl acetate: 95/5) to give the desired product (4.6 g) as a diastereomeric mixture (cis/trans 1:1, yield: 86%).

A solution of the compound above as cis/trans mixture (4.6 g, 19.87 mmol) in anhydrous THF (50 mL) was added at room temperature to a suspension of NaH (73 mg, 1.987 mmol, 60% dispersion in mineral oil) in dry THF (10 mL), under nitrogen. After stirring for 2.5 h at 25° C., the mixture was quenched with water (50 mL) at 0° C. and extracted with diethyl ether. The organic layer was dried over $Na_2SO_4$, filtered and concentrated in vacuo to give an oily residue, containing the (±)-lactone and the (±)-trans-hydroxy ester. Separation by flash chromatography on silica gel (DCM/ethyl acetate: 98/2) yielded the (±)-lactone as a white solid (1.65 g, 87%) and (±)-the trans-hydroxy ester as a colourless oil (1.95 g, 80%).

Lactone: MS m/z (EI+): 202 (M+), 171, 157, 143, 128.

$^1$H NMR (300 MHz, $CDCl_3$): δ7.13 (1H, d), 7.05 (1H, dd), 6.99 (1H, d), 5.42 (1H, d), 3.15 (1H, ddd), 2.99 (1H, m), 2.88–2.72 (2H, m), 2.46–2.34 (1H, m), 2.34 (3H, s), 1.96 (1H, d), 1.86 (1H, ddt).

Trans-hydroxy ester: MS m/z (ESI+): 217 (MH+—$H_2O$), 185, 157.

$^1$H NMR (300 MHz, $CDCl_3$): δ7.15-7.02 (3H, m), 5.03 (1H, dd), 3.68 (3H, s), 3.09 (1H, ddd), 3.08-2.97 (1H, m), 2.85 (1H, ddd), 2.32 (3H, s), 2.29-2.18 (1H, m), 2.08-1.98 (2H, m), 1.79-1.67 (1H, m).

PREPARATION 3

(±)-6-methyl-12-oxa-tricyclo[8.2.1.0]trideca-2,4,6-trien-11-ol

A solution of (±)-6-methyl-12-oxa-tricyclo[8.2.1.0] trideca-2,4,6-trien-11-one (1.64 g, 8.12 mmol) in 40 mL of dry toluene (previously distilled over sodium benzophenone-ketyl) was cooled at −60° C., diisobutylaluminium hydride (8.12 mL, 1M solution in hexanes) was added dropwise and the mixture was stirred at this temperature for 1 h. The reaction mixture was treated at −50° C. with methanol (50 mL), then with a saturated solution of Rochelle's salt (80 mL) and allowed to reach room temperature. After stirring for 2 h, the organic layer was separated, the aqueous layer was repeatedly extracted with ethyl acetate and the combined organic extracts were dried over $Na_2SO_4$, filtered and concentrated in vacuo. Filtration of the resulting residue on a silica gel short pad (eluent: DCM/ethyl acetate 9/1) gave the title compound as a white solid (1.54 g, 94%).

MS m/z (ESI+): 187 (MH+—$H_2O$), 169, 159.

$^1$H NMR (300 MHz, $CDCl_3$): δ7.04 (1H, dd), 6.99 (1H, dd), 6.92 (1H, dd), 5.56 (1H, s), 5.20 (1H, d), 2.98 (1H, dt), 2.87 (1H, dt), 2.72-2.62 (1H, m), 2.64 (1H, s br), 2.54 (1H, m), 2.31 (3H, s), 2.16-2.05 (1H, m), 1.65-1.52 (1H, m), 1.63 (1H, d).

EXAMPLE 1

(±)-cis-1-methyl-7-[[4-(2,6-dichloro-phenyl)piperidin-1-yl)]methyl]-6,7,8,9-tetrahydro-5H-benzocyclohepten-5-ol A solution of 4-(2,6-dichloro-phenyl)-piperidine (772 mg, 2.94 mmol) in methanol (15 mL) was dropped at room temperature into a solution of (±)-6-methyl-12-oxa-tricyclo [8.2.1.0]trideca-2,4,6-trien-11-ol (200 mg, 0.98 mmol) in methanol (7 mL). The mixture was heated at 50° C. for 2 h and then allowed to cool at room temperature. Then, $NaBH_4$ (37.1 mg, 0.98 mmol) was added portionwise at 0° C. and vigorous stirring was maintained overnight. The reaction mixture was treated with water at 0° C. and extracted with ethyl acetate, the organic layer was dried over $Na_2SO_4$, filtered and concentrated in vacuo. Flash chromatography of the resulting residue (silica gel, DCM/isopropanol/conc. ammonium hydroxide: 100/4/0.1) afforded the pure title compound as a white solid (327 mg, 80%).

MS m/z (ESI+): 418 (MH+).

$^1$H NMR (300 MHz, $CDCl_3$): δ7.42 (1H, d), 7.29-7.23 (2H, m), 7.12 (1H, dd), 7.05 (1H, d), 7.01 (1H, dd), 5.03 (1H, d), 3.52 (1H, tt), 3.16 (1H, dd), 3.04-2.94 (2H, m), 2.74-2.58 (2H, m), 2.50 (1H, dd), 2.34 (3H, s), 2.27 (1H, m), 2.19-2.03 (6H, m), 1.59-1.40 (3H, m), 1.32 (1H, m), 0.90 (1H, m).

ENANTIOSELECTIVE SYNTHESIS

PREPARATION 4

Synthesis of borane-oxazaborolidine complex (R)tetrahydro-1-methyl-3,3-diphenyl-1H,3H-pyrrolo[1,2-c][1,3,2]oxazaborole-borane A solution of (R)-2-methyl-CBS-oxazaborolidine (8 mL, 8 mmol, 1M in toluene), under inert atmosphere, was charged with borane-methyl sulfide neat (0.96 mL, 9.6 mmol) at 20° C. The mixture was stirred for 65 min at 20° C. to ensure complete formation of the borane complex and was then slowly diluted with 27 mL of dry hexane. During the addition, the borane adduct began to crystallize. After stirring at −10° C. for 3 h, a white precipitate was collected by filtration, washed twice with 5 mL of dry hexane and then dried in vacuo (100 mBar, 20° C.) to constant weight (2.3 g, 98%, mp 120-124° C. decomposes with bubbling).

$^1$H NMR matched that reported in the literature (Mathre, J. Org. Chem., 58, 2880,(1993)).

PREPARATION 5

(S,S)-6-methyl-12-oxa-tricyclo[8.2.1.0]trideca-2,4,6-trien-11-one and (S,R)-trans-1-methyl-5-hydroxy-6,7,8,9-tetrahydro-5H-benzocycloheptene-7-carboxylic acid methyl ester Under a static atmosphere of argon, dry dichloromethane (6.3 mL, dried over 3A-molecular sieves) was cooled at −20° C. and the (R)-borane-oxazaborolidine complex prepared above (1.83 g, 6.28 mmol) was added all at once. A 1M solution of (±)-1-methyl-5-oxo-6,7,8,9-tetrahydro-5H-benzocycloheptene-7-carboxylic acid methyl ester (1.122 g, 4.83 mmol) in dichloromethane (4.8 mL), previously dried over 3A molecular sieves overnight, was dropped into the reaction mixture over a 20 min period, at −20° C. The mixture was stirred at this temperature for 1 h and, without warming, methanol (55 mL) precooled at −20° C. was added carefully. The solution was warmed at room temperature, stirred for 2.5 h and then concentrated in vacuo. The resulting residue was dissolved in methanol and concentrated again in vacuo (this operation was repeated three times). Flash chromatography (silica gel, DCM/ethyl acetate: 95/5) afforded the pure (S,R)-trans-hydroxy ester as an oil (395 mg, 70%) and the (S,S)-lactone impure. Further flash chromatography on silica gel (hexane/diethyl ether: 8/2) of the (S,S)-lactone gave the pure compound as a white solid (341 mg, 70%).

MS spectra and $^1$H NMR of enantiomerically pure title compounds matched those of the two corresponding racemates reported in the preparation 2.

Enantiomeric excesses of both the lactone and the trans-hydroxy ester were evaluated through HPLC analysis. Column: CHIRALCEL OD (250 mm×4.6 mm i.d.). Mobile phase: Hexane 90 EtOH 10 (v/v). Flow rate: 0.5 mL/min. Detection UV: 215 nm.

Injection Volume: 10 uL. Temperature: Ambient. Run-time: 35 min.

Lactone: (R,R)-enantiomer 19 min<0.2%
(S,S)-enantiomer 25 min>99.8%.

Trans-hydroxy ester: (S,R)-enantiomer 15 min 99.8%
(R,S)-enantiomer 16 min 0.2%.

PREPARATION 6

(S,S)-6-methyl-12-oxa-tricyclo[8.2.1.0]trideca-2,4,6-trien-11-ol

Optically pure (S,S)-6-methyl-12-oxa-tricyclo[8.2.1.0]trideca-2,4,6-trien-11-one (320 mg, 1.58 mmol) is reacted according to the same experimental procedure as in preparation 3 to give the title compound (290 mg, 90%).

MS spectrum and $^1$H NMR of enantiomerically pure title compound matched those reported for the corresponding racemate in the preparation 3.

EXAMPLE 2

(S,S)-cis-1-methyl-7-[[4-(2,6-dichloro-phenyl)piperidin-1-yl)]methyl]-6,7,8,9-tetrahydro-5-H-benzocyclohepten-5ol Optically pure (S,S)-6-methyl-12-oxa-tricyclo[8.2.1.0]trideca-2,4,6-trien-11-ol (290 mg, 1.42 mmol) is reacted according to the same experimental procedure as in example 1 to give (S,S)-cis-1-methyl-7-[[4-(2,6-dichloro-phenyl)piperidin-1-yl)]methyl]-6,7,8,9-tetrahydro-5-H-benzocyclohepten-5-ol (470 mg, 80%

MS spectrum and $^1$H NMR of enantiomerically pure title compound matched those reported for the racemate in the example 1.

The enantiomeric excess of the title compound was evaluated by HPLC analysis. Column: DAICEL CHIRALCEL OD (250 mm×4.6 mm i.d.). Mobile phase: Hexane 95 EtOH 5 (v/v). Flow rate: 0.9 mL/min. Detection UV: 215 nm. Injection Volume: 10 uL.

Temperature: Ambient. Run-time: 25 min.
(S,S)-enantiomer: 11.7 min>99.8%
(R,R)-enantiomer: 13.9 min<0.2%.
$[\alpha]^D = -38.7°$ (c=0.51,isopropanol, 25C).

Note: the absolute configuration of (S,S)-cis-1-methyl-7-[[4-(2,6-dichloro-phenyl)piperidin-1-yl)]methyl]-6,7,8,9-tetrahydro-5H-benzocyclohepten-5-ol has been determined from the X-Ray diffraction pattern of crystals of its hydrochloride salt.

The invention claimed is:
1. A process for the preparation of a compound of formula (I) which is a single diastereoisomer or part of a mixture of diastereoisomers in which one diastereoisomer is predominant

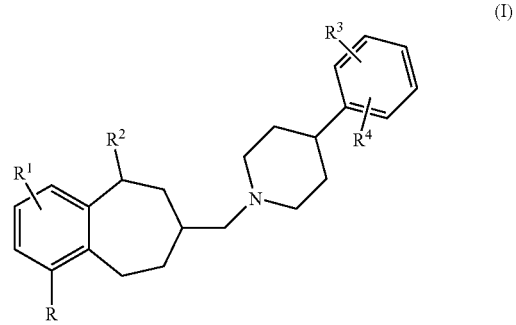

wherein:
R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, aryl$C_{1-6}$alkoxy, heteroaryl$C_{1-6}$alkoxy, amino$C_{1-6}$alkyl, ($C_{1-6}$ alkyl)amino$C_{1-6}$alkyl, di($C_{1-6}$alkyl)amino$C_{1-6}$alkyl, aryl$C_{1-6}$alkylamino, heteroaryl$C_{1-6}$alkylamino;

$R^1$ is hydrogen or R;

$R^2$ is hydroxy, $C_{1-6}$alkoxy, amino, $C_{1-6}$alkylamino, di($C_{1-6}$alkyl)amino;

$R^3$ and $R^4$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$alkoxy, $C_{1-6}$alkyl, amino, $C_{1-6}$alkylamino, or di($C_{1-6}$alkyl) amino;

and wherein any alkyl group or the alkyl moiety of any group containing such a moiety may be substituted one or more times by halo;

which comprises:

reacting a compound of formula (II) or (III),

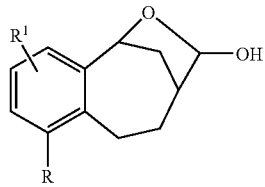
(II)

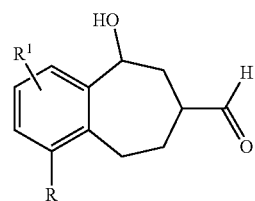
(III)

wherein:

R and $R^1$ are as hereinbefore defined for formula (I); which is a single diastereoisomer or part of a mixture of diastereoisomers in which one diastereoisomer is predominant, with a compound of formula (IV)

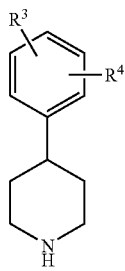
(IV)

wherein:

$R^3$ and $R^4$ are as hereinbefore defined for formula (I); and compounds of formula (II) and (III) are prepared from compounds of formula (V)

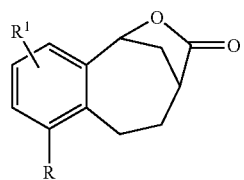
(V)

wherein:

R and R1 are as hereinbefore defined for formula (I), by reduction with a suitable reducing agent under reductive amination conditions with a suitable reducing agent or by catalytic hydrogenation.

2. A process according to claim 1 in which the compound of formula (V) is prepared from a compound of formula (VI)

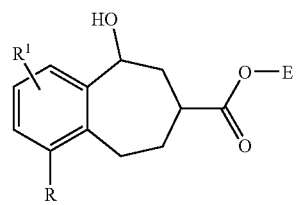
(VI)

wherein:

R and $R^1$ are as hereinbefore defined for formula (I) and E is $C_{1-6}$ alkyl; by reaction with an agent suitable to promote the intramolecular lactonization.

3. A process according to claim 2 in which the compound of formula (VI) is prepared from a compound of formula (VII):

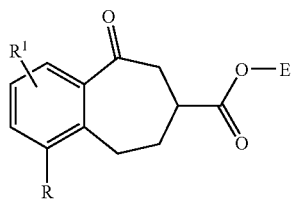
(VII)

wherein:

R and $R^1$ are as hereinbefore defined for formula (I) and E is $C_{1-6}$ alkyl; through reduction with a suitable reducing agent.

4. A process for the preparation of a compound of formula (I) which is a single enantiomer or part of a mixture of enantiomers in which one enantiomer is predominant

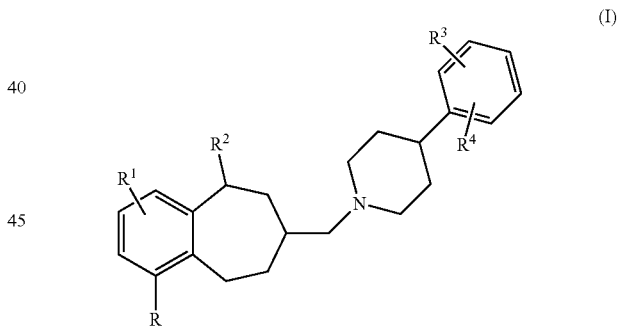
(I)

wherein:

R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, aryl$C_{1-6}$alkoxy, heteroaryl$C_{1-6}$alkoxy, amino$C_{1-6}$alkyl, ($C_{1-6}$alkyl)amino$C_{1-6}$alkyl, di($C_{1-6}$alkyl)amino$C_{1-6}$alkyl, aryl$C_{1-6}$alkylamino, heteroaryl$C_{1-6}$alkylamino;

$R^1$ is hydrogen or R;

$R^2$ is hydroxy, $C_{1-6}$alkoxy, amino, $C_{1-6}$alkylamino, di($C_{1-6}$alkyl)amino;

$R^3$ and $R^4$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$ alkoxy, $C_{1-6}$alkyl, amino, $C_{1-6}$alkylamino, or di($C_{1-6}$alkyl) amino;

and wherein any alkyl group or the alkyl moiety of any group containing such a moiety may be substituted one or more times by halo;

which comprises reacting a compound of formula (II) or (III) which is a single enantiomer or part of a mixture of enantiomers in which one enantiomer is predominant

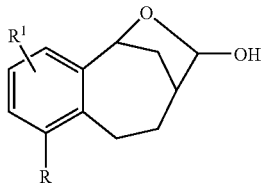

(II)

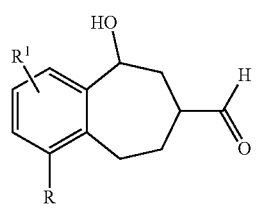

(III)

wherein:

R and $R^1$ are as hereinbefore defined for formula (I); with a compound of formula (IV)

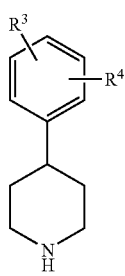

(IV)

wherein:

$R^3$ and $R^4$ are as hereinbefore defined for formula (I); and compounds of formula (II) and (III) are prepared from compounds of formula (V)

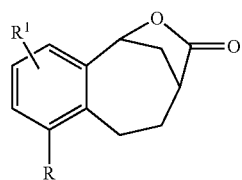

(V)

wherein:

R and R1 are as hereinbefore defined for formula (I), by reduction with a suitable reducing agent under reductive amination conditions with a suitable reducing agent or by catalytic hydrogenation.

5. A process according to claim 4 in which the compound of formula (V) is prepared from a compound of formula (VI) which is a single enantiomer or part of a mixture of enantiomers in which one enantiomer is predominant

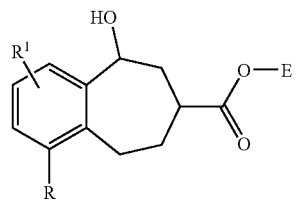

(VI)

wherein:

R and $R^1$ are as hereinbefore defined for formula (I) and E is $C_{1-6}$ alkyl;

by reaction with an agent suitable to promote the intramolecular lactonization.

6. A process according to claim 5 in which the compound of formula (VI) is prepared from a compound of formula (VII):

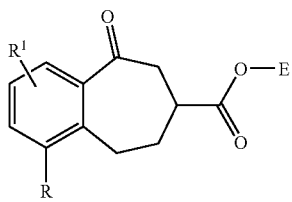

(VII)

wherein:

R and $R^1$ are as hereinbefore defined for formula (I) and E is $C_{1-6}$ alkyl; through reduction with a suitable borane-containing reducing agent in presence of a suitable chiral auxiliary.

7. A process according to claim 6 in which the chiral auxiliary is one of the chiral oxazaborolidine compounds:

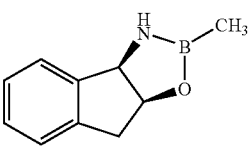

(IX)

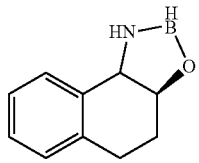

(X)

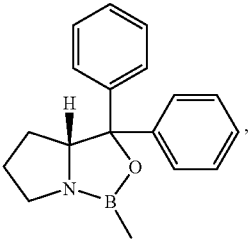

(XI)

* * * * *